Figure 1:
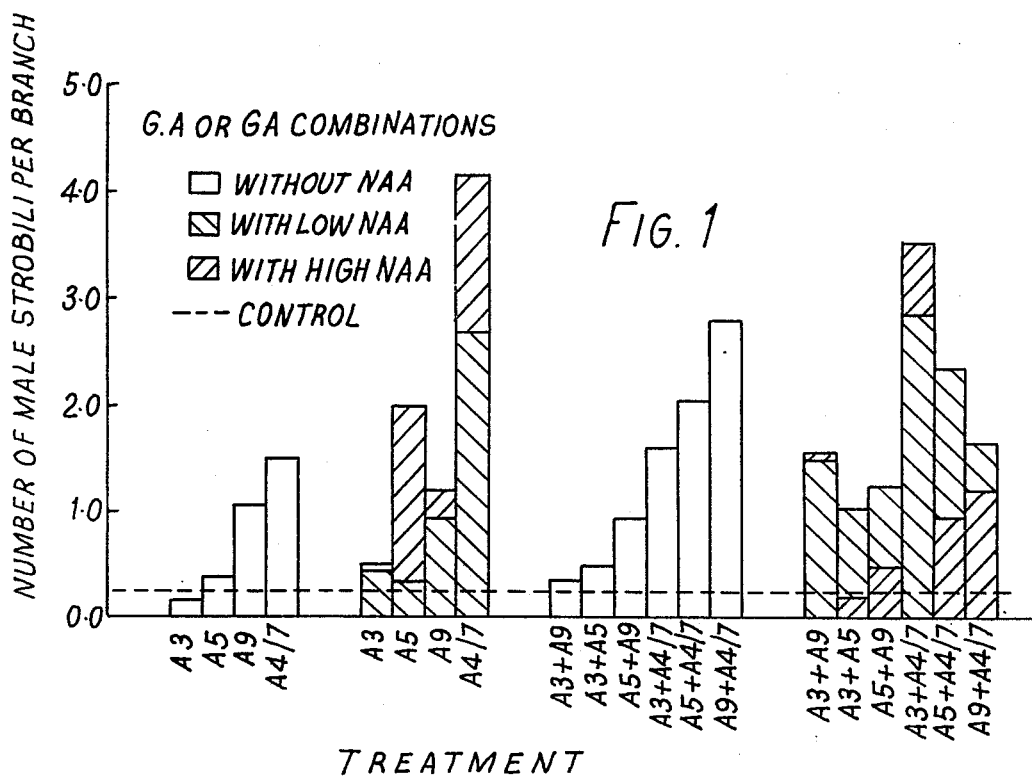

United States Patent [19]

Pharis

[11] 4,110,102

[45] Aug. 29, 1978

[54] METHOD AND COMPOSITION FOR TREATING TREES

[76] Inventor: Richard Persons Pharis, c/o University of Calgary, Calgary, Alberta, Canada

[21] Appl. No.: 667,977

[22] Filed: Mar. 18, 1976

[30] Foreign Application Priority Data

Apr. 3, 1975 [GB] United Kingdom ............... 13742

[51] Int. Cl.$^2$ ..................... A01N 9/02; A01N 5/00; A01N 9/24
[52] U.S. Cl. ......................................... 71/89
[58] Field of Search ................................... 71/89

[56] References Cited

U.S. PATENT DOCUMENTS

| | | | |
|---|---|---|---|
| 3,008,817 | 11/1961 | Nickell | 71/89 X |
| 3,038,794 | 6/1962 | Geary et al. | 71/89 X |
| 3,118,754 | 1/1964 | Nickell | 71/89 X |
| 3,137,562 | 6/1964 | Leben | 71/89 |
| 3,312,542 | 4/1967 | Kitzke et al. | 71/89 X |
| 3,506,434 | 4/1970 | Jacobi et al. | 71/89 |
| 3,679,392 | 7/1972 | Strauss et al. | 71/89 |
| 3,738,822 | 6/1973 | Asahi et al. | 71/89 |
| 3,810,750 | 5/1974 | Davidson et al. | 71/89 X |
| 4,009,021 | 2/1977 | Yih et al. | 71/89 X |
| 4,013,446 | 3/1977 | Beresky et al. | 71/89 X |

OTHER PUBLICATIONS

Ross et al., Abstract of Article "Gibberellin-Induced Flowering of Douglas-Fir Grafts" from Plant Physiology, vol. 51, Jun. 1973.

*Primary Examiner*—Joseph Paul Brust
*Attorney, Agent, or Firm*—Browdy and Neimark

[57] ABSTRACT

The formation of strobili is promoted in trees of the family Pinaceae by applying an auxin and one or more gibberellins selected from gibberellin $A_3$, gibberellin $A_4$, gibberellin $A_5$, giberellin $A_7$, gibberellin $A_9$ and gibberellin $A_{14}$. A preferred treatment comprises applying gibberellin $A_9$ and an auxin and compositions comprising these substances are also disclosed.

27 Claims, 6 Drawing Figures

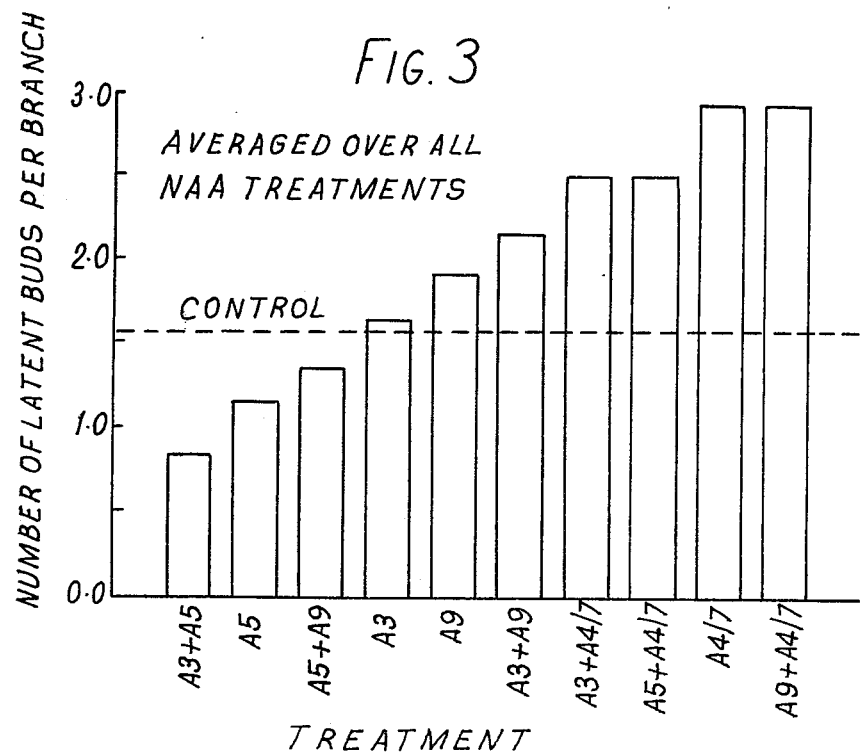
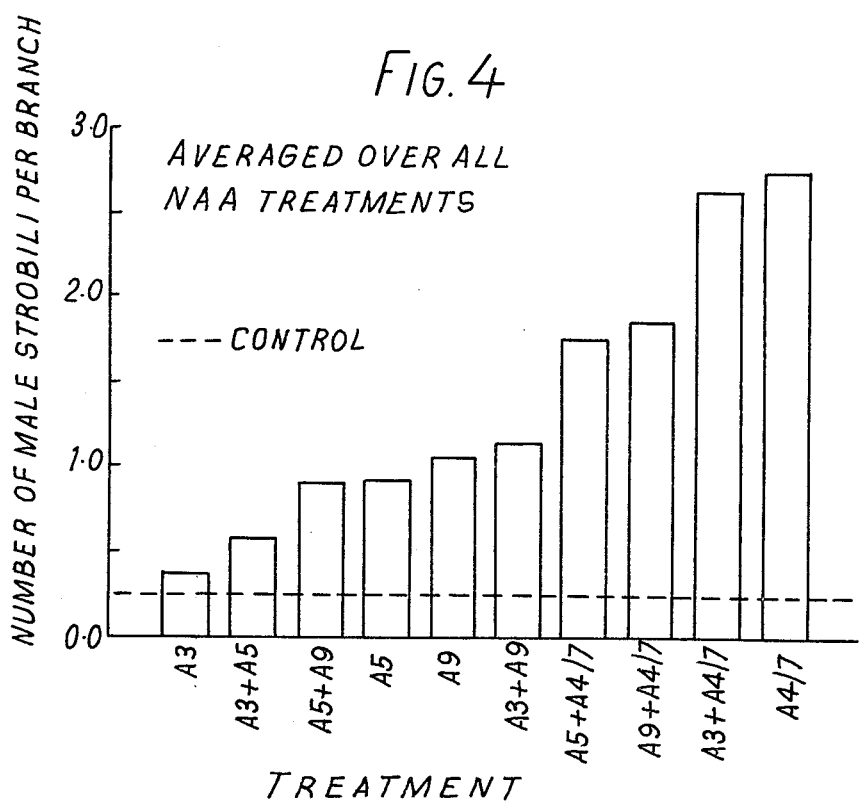

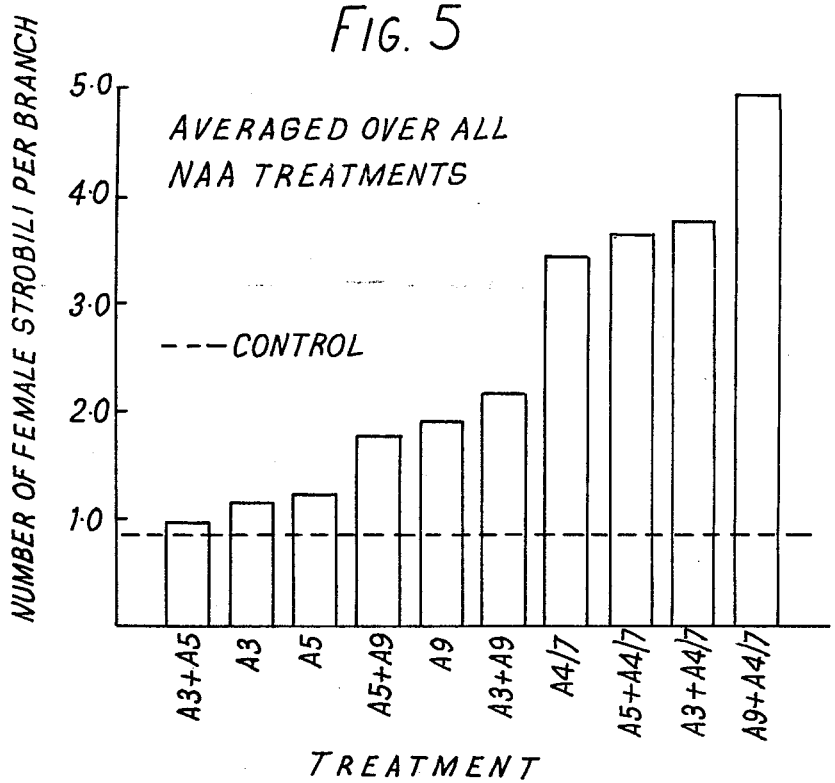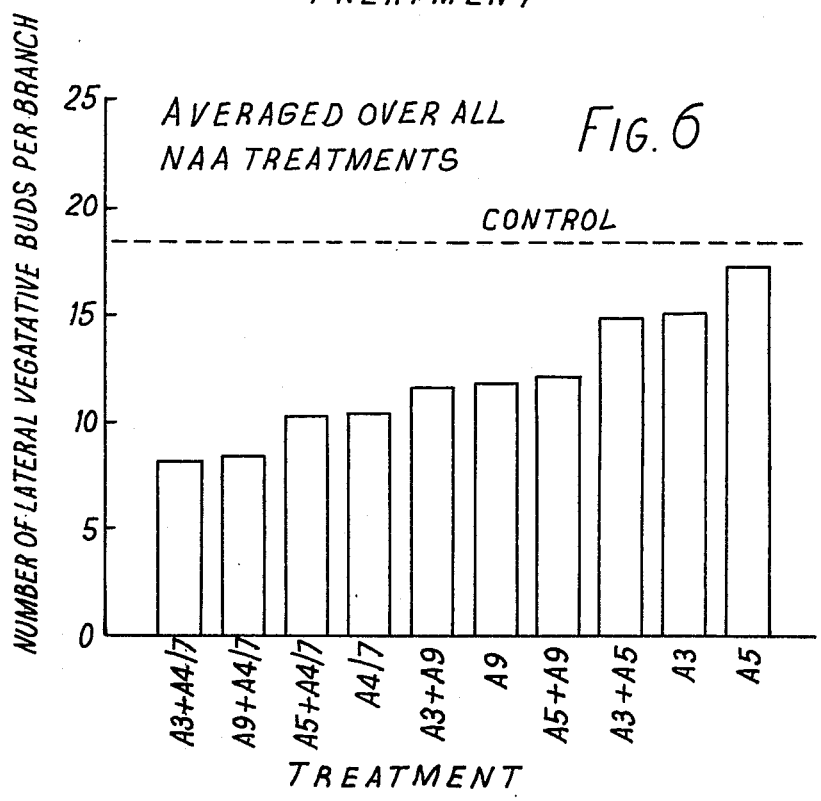

METHOD AND COMPOSITION FOR TREATING TREES

This invention relates to a method of treating trees of the family Pinaceae and to novel compositions useful in effecting the treatment.

Many species of the family Pinaceae do not flower and produce seed until they reach an age of more than 10 years. Thus, for example, seedling or grafted trees of Douglas fir, growing in a region noted for excellent flowering of both conifers and fruit trees were observed to reach a productive flowering state only after some 12 to 18 years.

I have now discovered a treatment which is capable of promoting the formation of strobili in trees of the family Pinaceae.

According to the present invention, there is provided a method of treating trees of the family Pinaceae which comprises applying thereto, in an amount sufficient to promote the formation of strobili, an auxin and one or more gibberellins selected from gibberellin $A_3$, gibberellin $A_9$, gibberellin $A_4$, gibberellin $A_7$ and gibberellin $A_5$. The treatment of trees of the family Pinaceae in accordance with the present invention has the surprising effect of promoting flowering. Particularly the formation of strobili of both sexes in increased numbers, compared with controls, on relatively immature trees which had not reached a productive flowering state has been observed.

The timing of the treatment is not considered to be unduly critical, but generally should cover the time when sexual differentiation would be expected to occur, i.e. in spring. Preferably the treatment is effected on a plurality of occasions encompassing the expected period when sexual differentiation occurs. Thus, for example, the treatment may be repeated at intervals., for example of seven to fourteen days over a period of up to 14 weeks. The exact timing of the first such treatment will depend on local climatic conditions, but good results have been observed when the initial application of the gibberellin and auxin coincided with the time when the terminal buds of the trees being treated were just emerging from dormancy.

Although application of an auxin with only one gibberellin has been found to be effective in promoting the formation of strobili, a more pronounced promoting effect can be obtained by applying a combination of the gibberellins with the auxin. Specifically, combinations of gibberellin $A_3$ and gibberellin $A_{4/7}$ mixture and combinations of gibberellin $A_9$ and gibberellin $A_{4/7}$ mixture have been found to be particularly effective.

Only small quantities of the gibberellins need be applied to the trees in order to promote the formation of strobili and generally application at a rate of 0.5 to 15 mg, preferably 1.4 to 2.8 mg, per branch is sufficient to promote the formation of strobili to a statistically significant extent. In view of their toxic nature to plants, only very small quantities of auxin should be applied, e.g. a total amount of from 60 $\mu$g to 300 $\mu$g per branch. The most effective quantities are those at the lower end of this range and accordingly it is preferred to apply the auxin in a total amount of from 60 $\mu$g to 120 $\mu$g per branch.

As is well known, auxins are a large class of plant growth regulators of which, in addition to the naturally occurring auxin, indolyl acetic acid, numerous synthetic auxins are known, many being used commercially as herbicides. A particular example of a synthetic auxin which may be used is naphthalene acetic acid. Others are phenoxyalkanoic acids, including phenoxyacetic acids, for example 4-chloro-2-methylphenoxyacetic acid (MCPA), 2,4-dichlorophenoxyacetic acid (2,4D) and 2,4,5 trichlorophenoxyacetic acid (2,4,5-T); phenoxypropionic acids, for example 2-(4-chloro-2-methylphenoxy) propionic acid (CMPP or mecoprop) and 2-(2,4 dichlorophenoxy) propionic acid (2,4DP or dichlorprop); and phenoxybutyric acids, for example 4-(2,4-dichlorophenoxy) butyric acid (2,4-DB) and 4-(4-chloro-2-methylphenoxy) butyric acid (MCPB). A further class of auxins are the substituted benzoic acids, such as 2,4,5-trichlorobenzoic acid (TBA); 3,5 dichloro-2-methoxybenzoic acid (dicamba); 2,3,5 trichloro-6-methoxybenzoic acid (tricamba); and 3-amino-2,5-dichlorobenzoic acid (amiben). All the above acids are active in the form of their salts and esters, for example their sodium, potassium, ammonium, dimethylamine and ethanolamine salts, and their methyl, ethyl, propyl and butyl esters.

In carrying out the method of the invention, the gibberellins and auxins are preferably applied to the trees in the form of compositions comprising the gibberellins and auxins mixed with a suitable diluent or carrier. Thus for example the gibberellins and auxins may be dissolved or dispersed in a liquid and applied in the form of a spray or injected into the tree or branch for example by the so-called "hanging bottle" technique. A more pronounced promotion of the formation of strobili can be obtained if, in addition to applying gibberellins and auxins in the manner hereinbefore described, the branches being treated are also girdled in an overlapping but non-destructive fashion, and accordingly, in carrying out the method of the invention, the additional step of girdling the branches being treated is preferably carried out. Other cultural treatments, such as water stress and fertilizing with nitrate nitrogen can, when applied with the method of the invention, synergistically enhance the flowering.

Most conveniently, in carrying out the method of the invention both the gibberellin and the auxin are applied to trees in the form of a composition comprising both substances. Compositions comprising gibberellin $A_9$ and an auxin in a weight ratio of from 40:1 to 5:1 which are particularly efficacious for use in carrying out the method of the invention, are novel and form a further aspect of the present invention. Preferred compositions, on account of their particularly high activity, comprise in addition gibberellin $A_{4/7}$ mixture.

Compositions according to the invention generally comprise the active ingredients mixed with a diluent or carrier. Preferably the compositions also comprise a surface-active agent to assist in spreading the compositions over the surface of plants to which they are applied.

Compositions according to the invention may be solid or liquid, and include both dilute compositions which are ready for immediate use, and concentrated compositions which require to be diluted before use. Preferably the compositions contain a total of from 0.01% to 90% by weight of the active ingredients. Dilute compositions ready for use preferably contain a total of from 0.01% to 2% of the active ingredients while concentrated compositions may contain a total of 10% to 90% of the active ingredients, although from 10% to 50% is usually preferred.

Solid compositions may be in the form of a powder, in which the active ingredients are mixed with a powdered solid diluent. Suitable solid diluents include for example, Fuller's earth, powdered kaolin, gypsum, chalk and kieselguhr. Such solid compositions may be applied as foliar dusts, or diluted with water and applied by spraying.

Another form of solid composition comprises the active ingredients in finely divided form together with a disintegrating agent, e.g. a mixture of citric acid and an alkali metal bicarbonate. Such a composition may be moulded into tablets, which when added to water disintegrate rapidly to form sprayable suspensions.

Liquid compositions may comprise solutions or dispersions of the active ingredients in water optionally containing a surface-active agent, or may comprise solutions or dispersions of the active ingredients in an organic diluent, which may optionally contain a surface-active agent. Another form of liquid composition comprises a solution of the active ingredients in a water-immiscible organic solvent which is dispersed as droplets in water.

Examples of surface-active agents which may be used in the compositions of the invention include the products of condensation of ethylene oxide with the following substances: alkyl substituted phenols such as octyl phenol and nonylphenol; sorbitan monolaurate; oleyl alcohol; and propylene oxide polymer. Other satisfactory surface-active agents include calcium dodecylbenzenesulphonate, and calcium, sodium, and ammonium lignosulphonates.

In one form of concentrated composition the active ingredients are finely divided and are dispersed in water in the presence of a surface-active agent and a suspending agent. Preferred suspending agents are those which impart thixotropic properties to and increase the viscosity of the concentrate. Examples of preferred suspending agents include hydrated colloidal mineral silicates, such as montmorillonite, beidellite, nontronite, hextorite, saponite, and saucorite. Bentonite is especially preferred. Other suspending agents include cellulose derivaties and polyvinyl alcohol.

The treatment of Douglas fir trees (*Pseudotsuga menziesii* var. *menziesii*) and lodgepole pine trees (*Pinus contorta*) in accordance with the method of the invention will now be described in the following Examples.

EXAMPLE 1

Six-year old Douglas fir seedlings growing on the Saanich penninsula of Vancouver Island which had not previously flowered were selected for testing.

Branches of generally similar strength and position on the trees were chosen at random either to serve as controls receiving no treatment or for treatment with various combinations of gibberellin $A_3$, gibberellin $A_{4/7}$ mixture, gibberellin $A_5$ and gibberellin $A_9$, and naphthalene acetic acid. In all, four branches were chosen on each tree. Except for a portion of the control branches, all of the branches were girdled with non-destructive overlapping half-moon girdles. (Although girdling alone has been shown to the ineffective in promoting flowering in grafted trees of this species, present results show that when the trees are girdled in addition to being treated with gibberellins and auxins in accordance with the invention, a more pronounced promotion of flowering is obtained than when ungirdled branches were similarly treated.)

Specifically the gibberellins referred to above were applied to respective branches singly, in combinations of two and in combination with two different quantities of naphthaleneacetic acid. Each treatment was applied to at least twenty branches selected at random on each of 10 half-sib families of trees. The terminal shoot was never treated.

The gibberellins and mixtures thereof with naphthaleneacetic acid were applied as a solution in 60 to 80% ethanol to the branch surface, with approximately one-half of the solution being applied to the new shoot after the shoot had "hardened" sufficiently.

Each treatment was repeated six times at intervals of approximately 2 weeks. 200 mg of each of the gibberellins referred to was applied at each treatment and where naphthaleneacetic acid (NAA) was applied in conjunction with the gibberellins, either a low (5 $\mu$g) or a high (25 $\mu$g) does was used. Inadvertently, for the first three treatments doses of 50 $\mu$g and 250 $\mu$g of naphthaleneacetic acid were applied and subsequently, when toxicity symptoms became apparent, these doses were respectively lowered to the correct values 5 and 25 $\mu$g.

The following diary entries were recorded during the treatment period:

| | |
|---|---|
| April 12th | 1st treatment (required three days). |
| April 17th | Some vegetative buds beginning to elongate were observed. |
| April 24th | 2nd treatment (gibberellin $A_5$ applied at rate of 100$\mu$g/branch owing to the limited availability of this substance. |
| May 8th | 3rd treatment (some vegetative buds actively flushing) - girdles not grown over. 100% $NH_4NO_3$ fertilizer applied at rate of 200 lb./acre. |
| May 22nd | 4th treatment. Toxic effect noted on plants treated with NAA (needles on older portion of shoot turning yellow). NAA dosage reduced to 5 and 25$\mu$g/branch. |
| May 30th | A few new shoots were observed to have lateral buds. |
| June 11th | 5th treatment. Where the new shoot was quite strong in appearance, one-half (i.e. 100$\mu$g) of the gibberellins (but not the NAA) was deposited along the new shoot on about one-quarter of the branches. |
| June 19th | 6th treatment - one-half (i.e. 100$\mu$g) of the gibberellins was applied to new shoot together with the other half as microdrops on the visible lateral buds of the new shoot. |

The trees were then left until strobili had formed, and male and female strobili on each branch were counted in January and again in April. The total numbers of latent buds and lateral vegetative buds on each branch were also determined.

The average numbers of male and female strobili per branch are set forther in tabular form against each treatment in the following Tables 1 and 2. In the tables the abbreviations $A_3$, $A_5$, $A_{4/7}$ and $A_9$ refer to the gibberellins $A_3$, $A_5$, $A_{4/7}$ and $A_9$. The symbols H and L in the columns headed "Naphthalene Acetic Acid" refer to the high and low doses described above.

Figure 2:
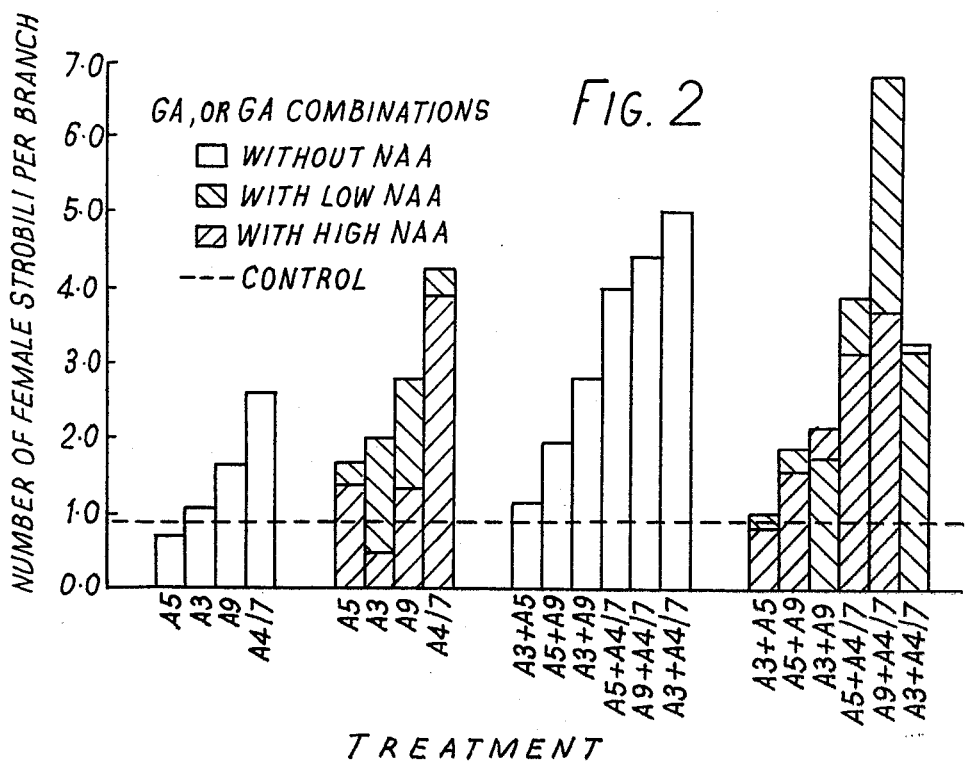

The results given in Tables 1 and 2 are presented in graphical form in FIGS. 1 and 2 of the accompanying drawings and a further graphical representation of the same results is given in FIGS. 3, 4, 5 and 6 of the drawings which shows the average results for all the treatments involving the use of naphthaleneacetic acid. Where, in the following Tables a different arrangement of asterisks appears under the heading "Significance" for any two values under the heading "Average No. of Male (or Female) Strobili/Branch", the difference between these values is statistically significant, i.e. there is a statistically significant difference between two values where one or more of the vertical columns of asterisks does not overlap the horizontal rows containing the values in question.

TABLE 1

| Gibberellin | Naphthalene Acetic Acid | Average No. of Male Strobili/Branch | Significance |
|---|---|---|---|
| $A_3$ | — | 0.15 | * |
| $A_3+A_5$ | H | 0.20 | * * |
| Control | — | 0.25 | * * * |
| $A_5$ | L | 0.35 | * * * |
| $A_3+A_9$ | — | 0.35 | * * * |
| $A_5$ | — | 0.40 | * * * |
| $A_3$ | L | 0.45 | * * * |
| $A_3$ | H | 0.50 | * * * |
| $A_3+A_5$ | — | 0.50 | * * * |
| $A_5+A_9$ | H | 0.50 | * * * |
| $A_9$ | L | 0.95 | * * * * |
| $A_5+A_{4/7}$ | H | 0.95 | * * * * |
| $A_5+A_9$ | — | 0.95 | * * * * |
| $A_9$ | — | 1.05 | * * * * |
| $A_3+A_5$ | L | 1.05 | * * * * |
| $A_9$ | H | 1.20 | * * * * |
| $A_9+A_{4/7}$ | H | 1.20 | * * * * |
| $A_5+A_9$ | L | 1.25 | * * * * |
| $A_{4/7}$ | — | 1.50 | * * * * |
| $A_3+A_9$ | L | 1.50 | * * * * |
| $A_3+A_9$ | H | 1.55 | * * * * |
| $A_3+A_{4/7}$ | — | 1.60 | * * * * |
| $A_9+A_{4/7}$ | L | 1.65 | * * * * |
| $A_5$ | H | 2.00 | * * * * * |
| $A_5+A_{4/7}$ | — | 2.05 | * * * * * |
| $A_5+A_{4/7}$ | L | 2.35 | * * * * * |
| $A_{4/7}$ | L | 2.70 | * * * * * |
| $A_9+A_{4/7}$ | — | 2.80 | * * * * |
| $A_3+A_{4/7}$ | L | 2.85 | * * * |
| $A_3+A_{4/7}$ | H | 3.50 | * * |
| $A_{4/7}$ | H | 4.15 | * |

TABLE 2

| Gibberellin | Naphthalene Acetic Acid | Average No. of Female Strobili/Branch | Significance |
|---|---|---|---|
| $A_3$ | H | 0.45 | * |
| $A_5$ | — | 0.70 | * * |
| $A_3+A_5$ | H | 0.80 | * * |
| Control | — | 0.85 | * * |
| $A_3+A_5$ | L | 1.00 | * * * |
| $A_3$ | — | 1.05 | * * * * |
| $A_3+A_5$ | — | 1.15 | * * * * |
| $A_9$ | H | 1.30 | * * * * |
| $A_5$ | H | 1.35 | * * * * |
| $A_5+A_9$ | H | 1.50 | * * * * |
| $A_5$ | L | 1.65 | * * * * * * |
| $A_9$ | — | 1.65 | * * * * * * |
| $A_3+A_9$ | L | 1.70 | * * * * * * * |
| $A_5+A_9$ | — | 1.90 | * * * * * * * * |
| $A_5+A_9$ | L | 1.95 | * * * * * * * * |
| $A_3$ | L | 2.00 | * * * * * * * * |
| $A_3+A_9$ | H | 2.05 | * * * * * * * * |
| $A_{4/7}$ | — | 2.30 | * * * * * * * * * |
| $A_9$ | L | 2.80 | * * * * * * * * |
| $A_3+A_9$ | — | 2.80 | * * * * * * * * |
| $A_3+A_{4/7}$ | L | 3.10 | * * * * * * * * |
| $A_5+A_{4/7}$ | H | 3.10 | * * * * * * * |
| $A_3+A_{4/7}$ | H | 3.25 | * * * * * * |
| $A_9+A_{4/7}$ | H | 3.65 | * * * * * |
| $A_5+A_{4/7}$ | L | 3.85 | * * * * |
| $A_{4/7}$ | H | 3.90 | * * * * |
| $A_5+A_{4/7}$ | — | 4.00 | * * * |
| $A_{4/7}$ | L | 4.25 | * * |
| $A_9+A_{4/7}$ | — | 4.40 | * * |
| $A_3+A_{4/7}$ | — | 5.00 | * |
| $A_9+A_{4/7}$ | L | 6.80 | |

EXAMPLE 2

A similar experiment to that described in Example 1 was carried out using lodgepole pine seedlings (*Pinus contorta*). The gibberellins tested were gibberellins $A_3$, $A_{4/7}$ mixture, $A_5$ and $A_9$. The auxins used were naphthaleneacetic acid and indolyl acetic acid.

The numbers of female strobili were counted and the results shown in the following Tables 3, 4 and 5. In Table 3 the results obtained in the tests using gibberellins $A_3$, $A_{4/7}$ mixture and a combination of these substances is presented. The results presented in the columns headed (1) relate to strobili detected by dissection in the autumn and the results presented in the columns headed (2) relate to the total numbers of strobili detected by dissection in the autumn and observed in the spring.

In Tables 4 and 5 the combined results of the specified treatments are presented.

TABLE 3

| Treatment | No. of Plants with Strobili/ Total No. of Plants | | Percentage of Plants Flowering | |
|---|---|---|---|---|
| | (1) | (2) | (1) | (2) |
| Control | 1/8 | 6/26 | 12.5 | 23.0 |
| $A_3$ | 0/3 | 0/7 | 0 | 0 |
| $A_{4/7}$ | 1/3 | 2/7 | 33.3 | 28.5 |
| $A_3+A_{4/7}$ (theoretical) | 0.6/4 | 1/8 | 16.6 | 14.2 |
| $A_3+A_{4/7}$ (actual) | 4/4 | 6/8 | 100.0 | 75.0 |

The results marked "theoretical" are values calculated from the results of treatment in which gibberellins $A_3$ and $A_{4/7}$ were applied separately on the basis that the observed effect would be additive in nature. The results marked "actual" derive from observations of experiments in which a combination of gibberellins $A_3$ and $A_{4/7}$ was applied.

TABLE 4

| Treatment | No. of Plants with Strobili/ Total No. of Plants | Percentage of Plants Flowering |
|---|---|---|
| Control | 3/19 | 15.7 |
| $A_3$, $A_{4/7}$, $A_5$ or $A_9$ | 6/11 | 54.5 |
| $A_3$, $A_{4/7}$ or $A_5$ or any combination thereof | 8/17 | 47.0 |
| $A_3$, $A_{4/7}$, $A_5$ or $A_9$ or any combinations thereof | 9/30 | 30.0 |

TABLE 5

| Treatment | No. of Strobili/ No. of Trees | No. of Strobili/ Tree |
|---|---|---|
| Control | 9/26 | 0.35 |
| $A_3$, $A_{4/7}$ or $A_3+A_{4/7}$ (each with 10μg IAA or NAA) | 32/52 | 0.62 |
| $A_3+A_{4/7}$ alone or with 10μg IAA or NAA | 29/32 | 0.91 |
| $A_3$, $A_{4/7}$ or $A_3+A_{4/7}$ (each with 100μg IAA or NAA,) IAA, NAA or IAA+NAA (10 and 100μg) | 18/85 | 0.21 |

The results set forth above illustrate the effect of the treatment according to the invention of promoting flowering of trees of the family Pinaceae. It is to be noted that the age of the trees was selected so that a low level of flowering might have been expected; also the geographical location (in the case of the Douglas fir experiments) favoured early flowering (i.e. the Saanich Penninusla on southern Vancouver Island is in a rain shadow and is noted for its high productivity of orchard trees and conifer cones). Nevertheless, a statistically significant promoting effect compared to the controls was observed in the trees treated in accordance with the method of the invention and other experiments with younger seedlings indicate that even where trees are otherwise too young to flower, the treatment of the invention is still efficacious and promotes flowering significantly above control levels.

In view of the possibility of reducing the age at which conifers are able to produce seed, the process of the invention is particularly valuable when applied to conifers within the family Pinaceae which do not flower until they are 10, 15 or even 25 + years of age and, for example, would allow forest tree geneticists to embark on programmes of tree improvement research which would otherwise be impractical. The end result of such research would of course be the production of genetically superior trees from which seed could be produced for reforestation and afforestation projects.

In addition to assisting in breeding programmes, preliminary results (from work where exogenous application of a mixture of an auxin and gibberellin $A_{4/7}$ promoted flowering in previously non-flowering Douglas fir grafts) indicate that exogenous application of this mixture can not only promote flowering in terms of number of strobili per branch (or plant), but may also enhance seed yield on a per cone basis. It is thus conceivable that application of optimal amounts of gibberellin auxin mixture in accordance with the method of the invention may increase seed yield on a 30–50 fold basis. Should this be the case, use of these treatments could enable large scale production of genetically superior seed (i.e. the resulting progeny are superior in growth rate, fibre length, progeny, disease resistance, etc.). The economic import of such increases in seed yield is considerable in view of the current world-wide demand for seedlings and seed to regenerate cut-over or burned forested land, or to afforest or reforest submarginal agriculture land.

Further examples of species of the family Pinaceae which may be treated in accordance with the method of the invention include the species *glauca, macrocarpa* and *taxifolia* of the genus Pseudotuga; the species *attenuata, banksiana, contorta, coulteri, densiflora, elliottii, jeffreyi, lambertiana, monticola, nigra, palustris, pinaster, ponderosa, radiata, strobus, sylvestris, taeda* and *virginiana* of the genus Pinus; the species *alba, amabilis, balsamea, concolor, grandsii, lasiocarpa, nobilis, procera* and *sibirica* of the genus Abies; the species *decidua, decidua X eurolepis, laricina, leptolepis* and *occidentalis* of the genus Larix, the species *abies, engelmannii, excelsa, glauca, mariana, pungens, rubens, rubra, sitchensis* and *smithiana* of the genus Picea; and the species *canadensis, heterophylla, mertensiana* and *sieboldi* of the genus Tsuga, as well as hybrids thereof.

It is of further note that since, in the experiments described above, control branches existed on the same trees as treated branches, movement of the treatment effect from treated branches to control branches undoubtedly increased the level of flowering even in the control branches.

I claim:

1. A method of inducing the formation of strobili in trees of the family Pinaceae which comprises applying thereto a strobili-formation-inducing effective amount of an auxin and one or more gibberellins selected from gibberellins $A_3$, $A_4$, $A_5$, $A_7$, $A_9$ and $A_{14}$, the auxin being applied in a non-toxic amount and in a weight ratio to the gibberellin or gibberellins of at least 1 part by weight of auxin per 250 parts by weight of gibberellin, said auxin being selected from the group consisting of indolyl acetic acid, naphthalene acetic acid; phenoxyacetic acids; phenoxy-propionic acids; phenoxybutyric acids; chlorine-substituted benzoic acids; salts thereof selected from sodium, potassium, ammonium, dimethylamine and ethanolamine salts and esters thereof selected from methyl, ethyl, propyl and butyl esters.

2. A method according to claim 1 in which an auxin, gibberellin $A_{4/7}$ mixture and gibberellin $A_5$ are applied to the trees.

3. A method according to claim 1 in which the auxin is naphthalene acetic acid.

4. A method of inducing the formation of strobili on trees of the family Pinaceae which comprises applying thereto a strobili-formation-inducing effective amount of an auxin and one or more gibberellins selected from gibberellins $A_3$, $A_4$, $A_7$, $A_9$ and $A_{14}$, the auxin being applied in a non-toxic amount and in a weight ratio to the gibberellin or gibberellins of at least 1 part by weight of auxin per 250 parts by weight of gibberellin, said auxin being selected from the group consisting of indolyl acetic acid, naphthalene acetic acid; phenoxyacetic acids; phenoxy-propionic acids; phenoxybutyric acids; chlorine-substituted benzoic acids; salts thereof selected from sodium, potassium, ammonium, dimethylamine and ethanolamine salts and esters thereof selected from methyl, ethyl, propyl and butyl esters.

5. A method according to claim 4 in which an auxin, gibberellin $A_{4/7}$ mixture and gibberellin $A_3$ are applied to the trees.

6. A method according to claim 4 in which an auxin, gibberellin $A_9$ and gibberellin $A_3$ are applied to the trees.

7. A method of inducing the formation of strobili in trees of the family Pinaceae which comprises applying thereto a strobili-formation-inducing effective amount of an auxin and one or more gibberellins selected from gibberellins $A_3$, $A_4$, $A_5$, $A_7$, $A_9$ and $A_{14}$, the auxin being applied in a non-toxic amount and in a weight ratio to the gibberellin or gibberellins of at least 1 part by weight of auxin per 250 parts by weight of gibberellin, said auxin being selected from the group consisting of aryl-or aryloxy-substituted alkanoic acids containing up to 12 carbon atoms and wherein the aryl portion of said substituent is selected from the group consisting of phenyl and naphthyl; salts thereof selected from sodium, potassium, ammonium, dimethyl amine and ethanol amine salts and esters thereof selected from methyl, ethyl, propyl and butyl esters.

8. A method in accordance with claim 7, in which the treatment is effected on a plurality of occasions encompassing the period when sexual differentiation of the trees would be expected to occur.

9. A method in accordance with claim 7, in which from 0.5 to 15 mg of gibberellin is applied to each treated branch, and from 60 to 300 $\mu$g of auxin is applied to each treated branch.

10. A method of inducing the formation of strobili on trees of the family Pinaceae which comprises applying thereto a strobili-formation-inducing effective amount of an auxin and one or more gibberellins selected from gibberellins $A_4$, $A_7$ and $A_9$, the auxin being applied in a non-toxic amount and in a weight ratio to the gibberellin or gibberellins of at least 1 part by weight of auxin per 250 parts by weight of gibberellin in which the auxin is selected from the group consisting of indolyl acetic acid, naphthalene acetic acid; phenoxyacetic acids; phenoxy-propionic acids; phenoxybutyric acids; chlorine-substituted benzoic acids; salts thereof selected from sodium potassium, ammonium, dimethylamine and ethanolamine salts and esters thereof selected from methyl, ethyl, propyl and butyl esters.

11. A method according to claim 10 in which an auxin and gibberellin $A_{4/7}$ mixture are applied to the trees.

12. A method according to claim 2 in which an auxin, gibberellin $A_{4/7}$ mixture and gibberellin $A_9$ are applied to the trees.

13. A method according to claim 10 in which an auxin and gibberellin $A_9$ are applied to the trees.

14. A method according to claim 10 in which a mixture comprising both the auxin and the gibberellin or gibberellins are applied to the trees.

15. A method according to claim 10 in which the treatment is effected on a plurality of occasions encompassing the period when sexual differentiation of the trees would be expected to occur.

16. A method according to claim 10 in which from 0.5 to 15 mg of gibberellin is applied to each treated branch.

17. A method according to claim 10 in which from 60 to 300 μg of auxin is applied to each treated branch.

18. A method according to claim 10 in which the trees being treated are of the genus Pseudotsuga.

19. A method according to claim 18 in which the trees being treated are of the species *Pseudotsuga menziesii*.

20. A method according to claim 10 in which the trees being treated are of the genus Pinus.

21. A method according to claim 20 in which the trees being treated are of the species *Pinus contorta*.

22. A method in accordance with claim 10 wherein said gibberellins are applied at the rate of 1.4 to 2.8 mg. per branch, and said auxin is applied at the rate of 60 μg to 120 μg per branch.

23. A method in accordance with claim 10 further comprising girdling the branches to which said gibberellins and auxin are applied in an overlapping but non-destructive fashion.

24. A method in accordance with claim 10 further comprising fertilizing said trees with nitrate fertilizer.

25. A method in accordance with claim 10 wherein the weight ratio of said auxin to said gibberellin is 1:5 to 1:40.

26. A composition for inducing the formation of strobili on trees of the family Pinaceae comprising gibberellin $A_9$ and an auxin in a weight ratio of 40:1 to 5:1 in which the auxin is selected from the group consisting of indolyl acetic acid, naphthalene acetic acid; phenoxyacetic acids; phenoxy-propionic acids; phenoxybutyric acids; chlorine-substituted benzoic acids; salts thereof selected from sodium, potassium, ammonium, dimethylamine and ethanolamine salts and esters thereof selected from methyl, ethyl, propyl and butyl esters.

27. A composition according to claim 26 additionally comprising gibberellin $A_{4/7}$ mixture.

* * * * *